United States Patent [19]

Ray

[11] 4,283,421

[45] Aug. 11, 1981

[54] ANTI-VIRAL TREATMENT

[76] Inventor: Frank F. Ray, 11449 S. Iroquois Dr., Phoenix, Ariz. 85044

[21] Appl. No.: 105,129

[22] Filed: Dec. 19, 1979

[51] Int. Cl.$^3$ .................. A61K 31/19; A61K 31/14
[52] U.S. Cl. .................................. 424/317; 424/329
[58] Field of Search .............................. 424/329, 317

[56] References Cited

U.S. PATENT DOCUMENTS

| 3,431,208 | 3/1969 | Bailey | 424/49 |
| 4,021,537 | 5/1977 | Sanriwo | 424/54 |

OTHER PUBLICATIONS

Chemical Abstracts 70:P4077g(1969).

*Primary Examiner*—Jerome D. Goldberg
*Attorney, Agent, or Firm*—Brown & Martin

[57] ABSTRACT

Anti-viral treatment, particularly treatment of herpes by application to infected areas of tissues of a composition from combination of alcohol solution by p-amino benzoic acid with aqueous solution of n-alkyl dimethyl benzyl ammonium chlorides or bromides and n-alkyl dimethyl athylbenzyl ammonium chlorides or bromides and a thickener to form a clear solution.

3 Claims, No Drawings

ANTI-VIRAL TREATMENT

FIELD OF THE INVENTION

This invention relates to anti-viral treatment and particularly to the treatment of the herpes virus.

BACKGROUND OF THE INVENTION

Virus infections both in man and in animals have long presented a serious problem to which no wholly satisfactory answer has been found. In particular, herpes infections, such as cold sores, canker sores and other more serious infections have been difficult to treat, particularly in moist sensitive areas, for example in gum and cheek areas within the mouth. Strong antiseptics and even antibiotics have not been found very effective. As is known, virus exists within cells so that treatment involves the two-fold problem of penetrating the cells with the agent and destruction of the virus by the agent.

SUMMARY OF THE INVENTION

It is an object of the present invention to provide an antiviral treatment useful even on sensitive surfaces for the treatment of certain virus infections.

I have found that a volatile solvent solution of the combination of p-Aminobenzoic Acid with a mixture of n-alkyl dimethyl benzyl ammonium chlorides or bromides and n-alkyl dimethyl ethylbenzyl ammonium chlorides or bromides is a useful agent for application in the treatment of virus infections such as herpes in humans and animals.

DETAILED DESCRIPTION OF THE INVENTION

According to the present invention, p-aminobenzoic acid, n-alkyl dimethyl benzyl ammonium chloride or bromide and n-alkyl dimethyl ethylbenzyl ammonium chloride or bromide are brought together in solution in a new cooperative relationship useful for the treatment of virus infections such as herpes.

p-Aminobenzoic acid, which is known for use as a bacterial screen for application to wounds and burns, but not as an anti-viral agent, is not soluble in water and is dissolved in a high proof volatile lower alcohol such as ethanol, methanol or isoproponol to form a clear solution. A preferred solution contains about 5% of p-aminobenzoic acid in 185 proof ethyl alcohol.

In the n-alkyl dimethyl benzyl ammonium chloride or bromide and n-alkyl dimethyl ethylbenzyl ammonium chloride or bromide, the n-alkyl groups are straight chain C-12 to C-18 groups, and the compounds, which are known as bactericides but not as anti-viral agents, are dissolved in water to form a clear solution. These components may be in the range of ratios of from about 35:65::65:35. Aqueous solutions, having a concentration of from about 0.125% to about 0.75% of the mixture of these have been found useful.

The active composition is formed by mixing the above solutions in relative quantities to provide from about 2.5 to about 15 parts of the second of the mixtures to 100 parts of the p-aminobenzoic acid. The mixture is a clear reddish liquid in which apparently the n-alkyl dimethyl benzyl ammonium chlorides and n-alkyl dimethyl ethylbenzyl ammonium chlorides act as carriers or dispersing agents so that the p-aminobenzoic acid is in a very fine, approximately molecular, dispersion in the water and alcohol vehicle.

Surprisingly, the components of this mixture cooperate to give anti-viral activity not suggested by the known properties of the individual components. No clear explanation of this unexpected cooperative action has been established, although it may be that the physical state to which the p-aminobenzoic acid has been brought enable it as well as n-alkyl dimethyl benzyl ammonium chloride and n-alkyl dimethyl ethylbenzyl ammonium chloride to reach the virus within a cell where the three components can cooperate to attack the virus. This explanation is advanced as of possible assistance in understanding the invention and it is to be understood that patentability is not dependent on its correctness.

A thickening agent, such as methyl cellulose (Methocel), or other suitable thickener is added to the mixed solutions to provide a viscosity for application to an affected area. It has been found that bringing the solution to a syrup-like consistency enables the deposition and absorption of an effective amount of the anti-viral agent when applied to an area infected with virus. It has been found, for instance, that application to a cold sore at an early stage will often effect cure within a day and application at a later stage will cause cure within about three days.

The following example is given to aid in understanding the invention and it is to be understood that the invention is not limited to the particular procedures, proportions or materials of the example.

EXAMPLE

Five ounces, dry measure, of p-amino benzoic acid was added to ninety five ounces liquid measure of 185 proof denatured ethyl alcohol which had been heated to 90° F. and the mixture was slowly stirred until solution was complete and clear.

To 96 ounces of water, there was added 2 ounces of a commercial bactericidal solution, containing 12.5% of n-alkyl (60% C-14, 30% C-16, 5% C-12, 5% C-18) dimethyl benzyl ammonium chlorides and 12.5% of n-alkyl (68% C-12, 32% C-14) dimethyl ethylbenzyl ammonium chlorides and the mixture was stirred slowly to prevent foaming until a clear solution was obtained.

The second solution was added slowly to the first solution while maintaining a temperature of 90° F. and the mixture was stirred slowly until it became clear.

To the mixed solutions there was added 1½ ounces of Methocel with stirring until it dissolved. The solution was then heated slowly to 120° F., removed from the heat and let stand for five minutes with stirring until the desired syrupy viscosity was achieved.

Having described my invention, what I claim is:

1. The method for treating viral infections in a human or animal host in need of said treatment which comprises contacting said host with an effective amount of a composition of matter comprising a mixture of a solution of 100 parts by weight of p-aminobenzoic acid in an amount of high proof volatile lower alcohol sufficient to dissolve and form a clear solution of said p-aminobenzoic acid and of a solution of from about 2.5 to about 15 parts by weight of a mixture of C-12 to C-18 n-alkyl dimethyl benzyl ammonium chlorides or bromides and C-12 to C-18 n-alkyl dimethyl ethylbenzyl ammonium chlorides or bromides in the range of relative proportions of 65:35::35:65 in an amount of water sufficient to dissolve said n-alkyl dimethyl ammonium chlorides or bromides and said n-alkyl dimethyl ethylbenzyl ammonium chlorides or bromides to form a clear solution.

2. The method for treating viral infections as defined in claim 1, in which said composition of matter comprises a mixture of 100 parts by weight of the solution of about 5 parts by weight of p-aminobenzoic acid in 95 parts by weight of 185 proof ethyl alcohol and about 100 parts by weight of an aqueous solution containing about 0.125 to about 0.75 parts by weight of said mixture of n-alkyl dimethyl benzyl ammonium chlorides and n-alkyl dimethyl ethylbenzyl ammonium chlorides.

3. The method for treating viral infections as defined in claim 2, in which said composition of matter comprises a thickening agent in amount to give a syrupy consistency.

* * * * *